United States Patent
Wikel

(10) Patent No.: US 10,314,831 B2
(45) Date of Patent: Jun. 11, 2019

(54) RAC1 INHIBITORS OF NEUROFIBROMA FORMATION

(71) Applicant: Indiana University Research and Technology Corporation, Indianapolis, IN (US)

(72) Inventor: James H. Wikel, Greenwood, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 15/108,595

(22) PCT Filed: Jan. 14, 2015

(86) PCT No.: PCT/US2015/011390
§ 371 (c)(1),
(2) Date: Jun. 28, 2016

(87) PCT Pub. No.: WO2015/108966
PCT Pub. Date: Jul. 23, 2015

(65) Prior Publication Data
US 2016/0317516 A1   Nov. 3, 2016

Related U.S. Application Data

(60) Provisional application No. 61/927,294, filed on Jan. 14, 2014.

(51) Int. Cl.
| | | |
|---|---|---|
| C07D 409/04 | (2006.01) |
| A61K 31/4436 | (2006.01) |
| A61K 31/255 | (2006.01) |
| A61K 31/381 | (2006.01) |
| A61K 31/4439 | (2006.01) |
| A61K 31/496 | (2006.01) |
| A61K 31/5377 | (2006.01) |

(52) U.S. Cl.
CPC ........ *A61K 31/4436* (2013.01); *A61K 31/255* (2013.01); *A61K 31/381* (2013.01); *A61K 31/4439* (2013.01); *A61K 31/496* (2013.01); *A61K 31/5377* (2013.01); *C07D 409/04* (2013.01)

(58) Field of Classification Search
CPC .................................................... C07D 409/04
USPC ....................................................... 546/280.4
See application file for complete search history.

(56) References Cited

FOREIGN PATENT DOCUMENTS

WO   2010119050 A1   10/2010

OTHER PUBLICATIONS

Dorwald, Side Reactions in Organic Synthesis 2005, Wiley:VCH Weinheim Preface, pp. 1-15 & Chapter *, pp. 279-308.*
Walters, et al., "Going further than Lipinski's rule in drug design," Expert Opin. Drug Discov., 2012, vol. 7, No. 2, pp. 99-107.
PUBCHEM SID-129545451 (Deposit date: Dec. 4, 2012) p. 3, structure.
PUBCHEM CID-2820661 (Create Date: Jul. 19, 2005) p. 3, structure.

* cited by examiner

*Primary Examiner* — Patricia L Morris
(74) *Attorney, Agent, or Firm* — Stinson Leonard Street LLP

(57) ABSTRACT

Small molecule inhibitor compounds for inhibiting Rac1 activity and their use for treating, preventing, or reducing the incidences of malignant and nonmalignant manifestations, e.g., plexiform neurofibromas that occur in subjects suffering from neurofibromatosis type 1 (NF1) are disclosed.

2 Claims, 6 Drawing Sheets

RAC1 INHIBITORS OF NEUROFIBROMA FORMATION

CROSS-REFERENCE TO RELATED APPLICATIONS

This application is based on and claims priority to International Publication Number WO 2015/108966 filed on Jan. 14, 2015, which is based on and claims priority to U.S. Provisional Patent Application No. 61/927,294 filed on Jan. 14, 2014, each of which is incorporated by reference herein in its entirety.

BACKGROUND OF THE DISCLOSURE

The present disclosure relates generally to small molecule inhibitor compounds for inhibiting Rac1 activity and their use for treating, preventing, or reducing the incidences of malignant and nonmalignant manifestations, e.g., plexiform neurofibromas that occur in subjects suffering from neurofibromatosis type 1 (NF1). More particularly, the present disclosure relates to small molecule inhibitor compounds that selectively inhibit Rac1 by blocking the interaction of Tiam1 guanine exchange factor (GEF) with the surface groove of Rac1 and to methods of administering these compounds to subjects suffering from NF1.

Mutations in the NF1 tumor suppressor gene cause neurofibromatosis type 1 (NF1), a common, pandemic human genetic disorder affecting approximately 1 in 3000 persons. NF1 encodes neurofibromin, a GTPase activating protein (GAP) for p21ras (Ras). Individuals with NF1 experience multiple malignant and nonmalignant manifestations, including plexiform neurofibromas, which affect 25-40% of NF1 patients and produce significant lifelong morbidity and mortality. Prior attempts to utilize standard chemotherapeutic approaches for treatment have failed, likely due to slow growth rates of the tumors. Surgery has been the mainstay of therapy, but gross total resections are difficult and recent institutional studies have shown relapse rates near 50%.

Taking both failures of surgery and traditional cytotoxic chemotherapy into account, many have investigated molecular inhibition of the Ras pathway as a treatment for plexiform neurofibromas. Targeting Ras activation directly proved challenging given its complex post-translational modification. Genetic or pharmacologic attenuation of Ras-directed signaling molecules in neurofibromin-deficient tumorigenic cells or in key lineages of the tumor microenvironment inhibited tumorigenesis. Utilizing a genetically-engineered murine model (GEMM) that consistently forms plexiform neurofibromas, small molecular inhibitors of receptor tyrosine kinase targets upstream of Ras signaling, specifically cKit, with imatinib mesylate were tested with relative success in these GEMMs. Additionally, imatinib mesylate was dispensed on a compassionate basis to a critically-ill 3 year old with an occlusive airway plexiform neurofibroma and within 3 months of treatment, the 3 year old had a 70% reduction in tumor volume along with resolution of all symptoms. Unfortunately, when imatinib mesylate was administered in a phase II clinical trial, 36% of patients suffered tumor progression and only 17% of patients had a measurable tumor response.

The RhoGTPase Rac1 was identified as a molecular mediator of pathological gain-in-function phenotypes in neurofibromin-deficient Schwann cells, mast cells, and monocyte-macrophages. Genetic Rac1 ablation in Schwann cells reduced the number of plexiform neurofibromas by 95%, as compared to intercrossed strains having a functionally intact Rac1 locus (FIG. 1). Rac1 disruption similarly mitigated pathological proliferation and migration of Nf1−/− Schwann cells in vitro. These data suggest that Schwann cells, the genetically established tumor cell of origin, depend on the hyperactivity within Ras-Rac-directed pathways and may serve as a target for therapy.

Accordingly, there is a need in the art for additional inhibitors of multiple receptor tyrosine kinases and additional targets downstream of Ras-GTP for use as molecular therapies for plexiform neurofibromas. It would be further advantageous if the inhibitors had reduced toxicity and greater pharmacological activity.

SUMMARY OF THE DISCLOSURE

The present disclosure relates generally to treating, preventing, and reducing the incidences of manifestations resulting from NF1. Particularly, the present disclosure is directed to small molecule inhibitor compounds that selectively inhibit Rac1 activity, which unexpectedly was found to reduce and/or eliminate plexiform neurofibroma development in NF1 individuals. Additionally, inhibition of Rac1 may also be a potential target in resistant leukemias, pancreatic cancers, and melanomas.

Accordingly, in one aspect, the present disclosure is directed to a compound for inhibiting Rac1. The compound comprises the structure of

A-B-C-D, wherein A is selected from the group consisting of pyridyl and phenyl;
B is selected from the group consisting of thiophene and phenyl;
C is selected from the group consisting of sulfur (S), sulfoxide (SO), sulfone ($SO_2$), sulfonate ($SO_3$), carboxylate ($CO_2$), $CH_2CH_2$, C(=O), and sulfonamide ($SO_2N$); and
D is selected from the group consisting of hydrogen, methyl, benzyl, phenyl, t-butyl, neopentyl, 3,5-dichlorophenyl, 4-methoxyphenyl, 2-chlorophenyl, 4-chlorophenyl, morpholino, piperdino, pyrrolidino, 4-methoxyphenyl, dimethylamino, 2-trifluoromethylphenyl, sulfonamidophenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl;
with the provisos that:
when A is pyridyl, B is thiophene, C is sulfonate ($SO_3$), D is selected from the group consisting of hydrogen, methyl, benzyl, phenyl, t-butyl, neopentyll, 2-chlorophenyl, morpholino, piperdino, pyrrolidino, 4-methoxyphenyl, dimethylamino, 2-trifluoromethylphenyl, sulfonamidophenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl;
when A is pyridyl, B is thiophene, C is sulfone ($SO_2$), D is selected from the group consisting of hydrogen, methyl, benzyl, phenyl, t-butyl, neopentyl, 3,5-dichlorophenyl, 4-methoxyphenyl, 2-chlorophenyl, 4-chlorophenyl, 4-methoxyphenyl, sulfonamidophenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl;
when A is pyridyl, B is thiophene, C is carboxylate ($CO_2$), D is selected from the group consisting of hydrogen, benzyl, phenyl, t-butyl, neopentyl, 2-chlorophenyl, 4-chlorophenyl, morpholino, piperdino, pyrrolidino, 4-methoxyphenyl, dimethylamino, 2-trifluoromethylphenyl, sulfonamidophenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl; and when A is pyridyl, B is thiophene, C is sulfonamide ($SO_2N$), D is selected from the group consisting of hydrogen, methyl, benzyl, phenyl, t-butyl, neopentyl, 3,5-dichlorophenyl, 4-methoxyphenyl, 4-chlorophenyl, morpholino, piperdino, pyrrolidino, 4-methoxyphenyl, dimethylamino, 2-trifluoromethylphenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl.

In another aspect, the present disclosure is directed to a method of treating neurofibromatosis type 1 in a subject in need thereof. The method comprises: administering to the subject a compound having the structure

A-B-C-D, wherein A is selected from the group consisting of pyridyl and phenyl; B is selected from the group consisting of thiophene and phenyl; C is selected from the group consisting of sulfur (S), sulfoxide (SO), sulfone ($SO_2$), sulfonate ($SO_3$), carboxylate ($CO_2$), $CH_2CH_2$, C(=O), and sulfonamide ($SO_2N$); and D is selected from the group consisting of hydrogen, methyl, benzyl, phenyl, t-butyl, neopentyl, 3,5-dichlorophenyl, 4-methoxyphenyl, 2-chlorophenyl, 4-chlorophenyl, morpholino, piperdino, pyrrolidino, 4-methoxyphenyl, dimethylamino, 2-trifluoromethylphenyl, sulfonamidophenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl.

In yet another aspect, the present disclosure is directed to method of treating plexiform neurofibromas in a subject in need thereof. The method comprises: administering to the subject a compound having the structure

A-B-C-D, wherein A is selected from the group consisting of pyridyl and phenyl; B is selected from the group consisting of thiophene and phenyl; C is selected from the group consisting of sulfur (S), sulfoxide (SO), sulfone ($SO_2$), sulfonate ($SO_3$), carboxylate ($CO_2$), $CH_2CH_2$, C(=O), and sulfonamide ($SO_2N$); and D is selected from the group consisting of hydrogen, methyl, benzyl, phenyl, t-butyl, neopentyl, 3,5-dichlorophenyl, 4-methoxyphenyl, 2-chlorophenyl, 4-chlorophenyl, morpholino, piperdino, pyrrolidino, 4-methoxyphenyl, dimethylamino, 2-trifluoromethylphenyl, sulfonamidophenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl.

In yet another aspect, the present disclosure is directed to method for inhibiting Rac1. The method comprises: administering a compound having the structure

A-B-C-D, wherein A is selected from the group consisting of pyridyl and phenyl; B is selected from the group consisting of thiophene and phenyl; C is selected from the group consisting of sulfur (S), sulfoxide (SO), sulfone ($SO_2$), sulfonate ($SO_3$), carboxylate ($CO_2$), $CH_2CH_2$, C(=O), and sulfonamide ($SO_2N$); and D is selected from the group consisting of hydrogen, methyl, benzyl, phenyl, t-butyl, neopentyl, 3,5-dichlorophenyl, 4-methoxyphenyl, 2-chlorophenyl, 4-chlorophenyl, morpholino, piperdino, pyrrolidino, 4-methoxyphenyl, dimethylamino, 2-trifluoromethylphenyl, sulfonamidophenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl.

In yet another aspect, the present disclosure is directed to a method of screening a candidate compound for Rac1 inhibiting activity. The method comprises: contacting a NF1-deficient Schwann cell with a candidate compound and analyzing Schwann cell proliferation. In some embodiments, the method further includes analyzing the inhibitory effect on Rac1-GTP.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 3A) Compound C20 inhibits PDGF-mediated Rac1-GTP activity at 0.5 µM in murine-derived neurofibroma cells. After 24-hour starvation in 0.5% BSA/DMEM, Nf1−/− Schwann cells were pretreated with compound C20 at the indicated concentrations. Cells were then stimulated with 50 ng/mL PDGF for 2 minutes and harvested for immunoprecipitation and activity assays. FIG. 3B) Compound C20 specifically interfered with Rac1-Tiam1 interactions at 15 nM in a GEF assay using purified protein. FIG. 3C) In [$^3$H]-thymidine dose-inhibition experiments, murine derived Nf1−/− Schwann cells were pre-treated with increasing quantities of the known Rac1 inhibitor NSC23766 or with putative Rac1 inhibitor C20. C20 demonstrated a dose-inhibition relationship with an approximate $IC_{50}$ of 2.0 µM.

Figure 1:
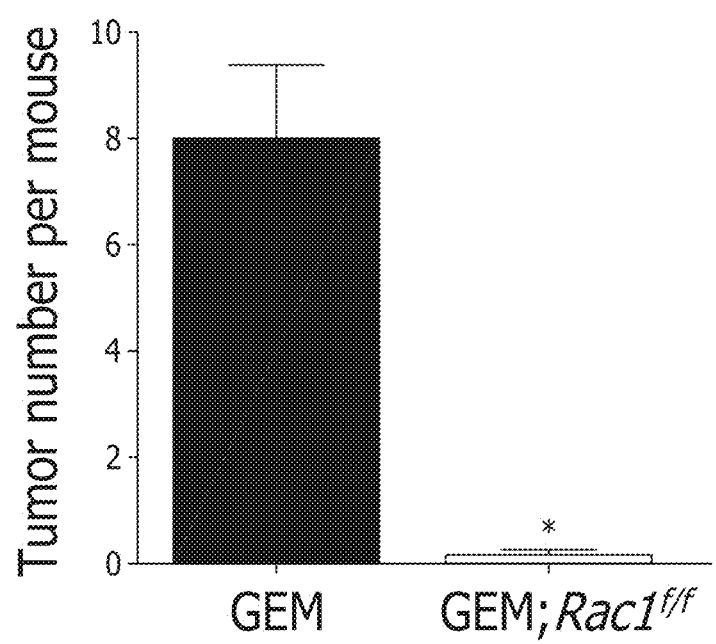
FIG. 1 depicts the effect of Rac1 disruption on tumor formulation in a GEMM of plexiform neurofibromas.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, small molecule inhibitor compounds of Rac1 are disclosed. The compounds have the general structure of

A-B-C-D, wherein A is selected from the group consisting of pyridyl and phenyl; B is selected from the group consisting of thiophene and phenyl; C is selected from the group consisting of sulfur (S), sulfoxide (SO), sulfone ($SO_2$), sulfonate ($SO_3$) (including for example, as A-B-$SO_2$-O-D and A-B-O—$SO_2$-D), carboxylate ($CO_2$) (including for example, as A-B-C(=O)—O-D and A-B-O-C(=O)-D), $CH_2CH_2$, C(=O), and sulfonamide ($SO_2N$) (including for example, as A-B-$SO_2$N-D and A-B-N—$SO_2$-D); and D is selected from the group consisting of hydrogen, methyl, benzyl, phenyl, t-butyl, neopentyl, 3,5-dichlorophenyl, 4-methoxyphenyl, 2-chlorophenyl, 4-chlorophenyl, morpholino, piperdino, pyrrolidino, 4-methoxyphenyl, dimethylamino, 2-trifluoromethylphenyl, sulfonamidophenyl, 4-sulfonamidophenyl, 4-trifluoromethylsulfonylphenyl, 3,4-dimethylphenyl, 3,5-methoxyphenyl, 3,5-difluorophenyl, 3,5-dicarboxamidophenyl, 3,5-dicyanophenyl, and 3,5-dimethylsufonylphenyl.

In some embodiments, the compounds have the general structure of

A-B-C-D, wherein A is pyridyl, B is thiophene, C is $SO_3$, and D is selected from the group consisting of phenyl, 3,5-dimethylphenyl, 3,5-methoxyphenyl, 3,5-difluorophenyl, 3,5-ditrifluoromethylphenyl, 3,5-dicarboxamidophenyl, 3,5-dicyanophenyl, 3,5-dimethylsufonylphenyl, 4-methoxyphenyl, 4-chlorophenyl, 4-sulfonamidophenyl, and 4-trifluoromethylsulfonylphenyl.

In other embodiments, the compounds have the general structure of

A-B-C-D, wherein A is pyridyl, B is thiophene, C is $SO_2$, and D is selected from the group consisting of morpholino, piperdino, pyrrolidino, dimethylamino, and 2-trifluoromethylphenyl.

In still other embodiments, the compounds have the general structure of

A-B-C-D, wherein A is pyridyl, B is thiophene, C is sulfonamide ($SO_2N$), and D is selected from the group consisting of 2-chlorophenyl and sulfonamidophenyl.

In still other embodiments, the compounds have the general structure of

A-B-C-D, wherein A is pyridyl, B is thiophene, C is $CO_2$, and D is selected from the group consisting of 3,5-dichlorophenyl, methyl, and 4-methoxylphenyl.

In one particularly suitable aspect, the small molecule inhibitor is C20-26 that blocks the interaction of Tiam1 guanine exchange factor (GEF) with the surface groove of Rac1 thereby inhibiting its activity. This small molecule inhibitor compound of the Rac1-Tiam1 interaction is significant because as seen in FIG. 1, ablation of Rac1 resulted in no plexiform neurofibroma development in an NF1 GEMM model. As discussed above, traditional chemotherapy has failed to treat this disease and there has been limited clinical success with targeted molecular inhibitors such as imatinib. Additionally, recent research has shown that Rac1 may be a potential target in resistant leukemias, pancreatic cancers, and melanoma. Aberrant Rac1 activation in numerous cancer subtypes broadens the potential use for a compound such as C20-26 or its analogs making it more attractive for further development.

Previous work was conducted into developing Rac1 inhibitors to identify small molecule inhibitors of Rac. One such inhibitor, NSC23766, required large micromolar concentrations (50 μM) to inhibit Rac1 (50 uM) and exhibited high toxicity. Additional compounds have not been able to achieve Rac1 inhibition at submicromolar concentrations. Another inhibitor, EHop-016 inhibited Rac1 at 1.1 μM concentration. Additionally EHop-016 specifically targets the interaction of Vav2, a GEF that also binds with Rho and Cdc42, and thus, lacks the specificity for the Rac1-specific GEF, Tiam 1, that C20-26 possesses. C20-26 vastly improves on the potency of Rac1 inhibition when compared to NSC23766 and other inhibitors. Particularly, C20-26 inhibits Rac1 at 40 nM, thus is 25 times more potent as the next best competitor EHop-016 and 250-fold more potent than NSC23766.

Interestingly, NSC23766 and C20-26 have completely different chemical structures, with a Tanimoto coefficient of molecular fingerprint similarity of 0.14 (with 1.0 representing identity). Therefore, while such a compound appears to selectively inhibit Rac1 activity, its unique structure, as compared to NSC23766, lends to the possibility for reduced toxicity and greater pharmacological activity.

Other suitable compounds for inhibiting Rac1 are shown in Table 1.

TABLE 1

| Compound | A/B | C | D |
|---|---|---|---|
| First SAR | | | |
| C20 | pyridyl/thiophene | $SO_3$ | 3,5-dichlorophenyl |
| C20-2 | pyridyl/thiophene | $CO_2$ | 3,5-dichlorophenyl |
| C20-8 | pyridyl/thiophene | $SO_3$ | 4-methoxyphenyl |
| C20-7 | pyridyl/thiophene | $SO_3$ | 4-chlorophenyl |
| C20-3 | pyridyl/thiophene | $CO_2$ | methyl |
| C20-4 | pyridyl/thiophene | $SO_2$ | morpholino |
| C20-5 | pyridyl/thiophene | $SO_2$ | piperdino |
| C20-6 | pyridyl/thiophene | $SO_2N$ | 2-chlorophenyl |
| C20-11 | pyridyl/thiophene | $SO_2$ | pyrrolidino |
| C20-12 | pyridyl/thiophene | $CO_2$ | 4-methoxyphenyl |
| C20-13 | pyridyl/thiophene | $SO_2$ | dimethylamino |
| C20-1 | pyridyl/thiophene | $SO_2$ | 2-trifluoromethylphenyl |
| C20-10 | pyridyl/thiophene | $SO_2N$ | sulfonamidophenyl |
| C20-19 | m-phenyl/thiophene | $SO_3$ | 4-sulfonamidophenyl |
| Second SAR | | | |
| C20-23 | pyridyl/thiophene | $SO_3$ | 4-trifluoromethylsulfonylphenyl |
| C20-24 | pyridyl/thiophene | $OSO_2$ | 3,5-dichlorophenyl |
| C20-25 | pyridyl/m-phenyl | $SO_3$ | 3,5-dichlorophenyl |
| C20-26 | pyridyl/thiophene | $SO_3$ | Phenyl |
| C20-27 | pyridyl/thiophene | $SO_3$ | 3,5-dimethylphenyl |
| C20-28 | pyridyl/thiophene | $SO_3$ | 3,5-methoxyphenyl |
| C20-29 | pyridyl/thiophene | $SO_3$ | 3,5-difluorophenyl |
| C20-30 | pyridyl/thiophene | $SO_3$ | 3,5-ditrifluoromethylphenyl |
| C20-31 | pyridyl/thiophene | $SO_3$ | 3,5-dicaroxamidophenyl |
| C20-32 | pyridyl/thiophene | $SO_3$ | 3,5-dicyanophenyl |
| C20-33 | pyridyl/thiophene | $SO_3$ | 3,5-dimethylsufonylphenyl |
| Third SAR | | | |
| C20-34 | pyridyl/thiophene | $SO_3$ | hydrogen |
| C20-35 | pyridyl/thiophene | $SO_2$ | phenyl |
| C20-36 | pyridyl/thiophene | $SO_2$ | benzyl |
| C20-37 | pyridyl/thiophene | $CH_2CH_2$ | phenyl |
| C20-38 | pyridyl/thiophene | C(=O) | phenyl |
| C20-39 | pyridyl/thiophene | S | phenyl |
| C20-40 | pyridyl/thiophene | SO | phenyl |
| C20-41 | phenyl/phenyl | $SO_3$ | t-butyl |
| C20-42 | pyridyl/thiophene | $SO_3$ | neopentyl |

TABLE 1-continued

| Compound | A/B | C | D |
|---|---|---|---|
| C20-43 | phenyl/m-phenyl | SO$_3$ | phenyl |
| C20-44 | phenyl/p-phenyl | SO$_3$ | phenyl |
| C20-45 | phenyl/o-phenyl | SO$_3$ | phenyl |

In another aspect, the present disclosure is directed to treating, preventing, and/or reducing the incidences of malignant and nonmalignant manifestations of neurofibromatosis type 1 (NF1), and in particular aspects, plexiform neurofibromas in a subject in need thereof. As used herein, "a subject in need thereof" refers to a subject diagnosed by one skilled in the art such as, for example, a clinician, having or being at risk of neurofibromatosis type 1 (NF1), or having or being at risk of having malignant or nonmalignant manifestations typically experienced by those suffering from NF1. As used herein, "at risk of" or "susceptible to" are used interchanging to refer to a subject that is more likely to have or develop a disease, condition, or disorder due to age, sex, family history, and/or lifestyle.

Generally, the methods for treating, preventing, and/or reducing incidences of NF1-associated manifestations include identifying a subject in need thereof, and administering to the subject, a therapeutically effective amount of a small molecule inhibitor compound having the structure of C20-26 or an analogue thereof.

The phrases "effective amount" or "therapeutically effective amount" of the compound of the disclosure are used interchangeably to refer to a sufficient amount of the compound to treat disorders, at a reasonable benefit/risk ratio applicable to any medical treatment. It can be understood, however, that the total daily usage of the compounds of the disclosure can be decided by the attending physician within the scope of sound medical judgment. The specific therapeutically effective dose level for any particular patient can depend upon a variety of factors including the disorder being treated and the severity of the disorder; activity of the specific compound employed; the specific pharmaceutical composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Actual dosage levels of compounds in the pharmaceutical compositions of this disclosure can be varied so as to obtain an amount of the compound(s) that is effective to achieve the desired therapeutic response for a particular patient, compositions and mode of administration. The selected dosage level can depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Particularly suitable subjects are humans. Suitable subjects can also be experimental animals such as, for example, monkeys and rodents.

EXAMPLES

Example 1

In this Example, compound C20 was isolated and its physical properties analyzed.

Specifically, C20 was identified using a ligand-based virtual screen using NSC23766 as a reference structure. An in silico design protocol required that a candidate compound pass the "Rule of 5" for drug design (Walters et al., "Going further than Lipinski's rule in drug design," Expert Opin. Drug Discov. 2012, 7(2):99-107) and was predicted to cross the blood-brain barrier. Multiple 3D shapes were generated and compared to that of NSC23766 to create a numerical similarity score between 0 and 1, with 1 signifying exact identity.

Figure 3A:
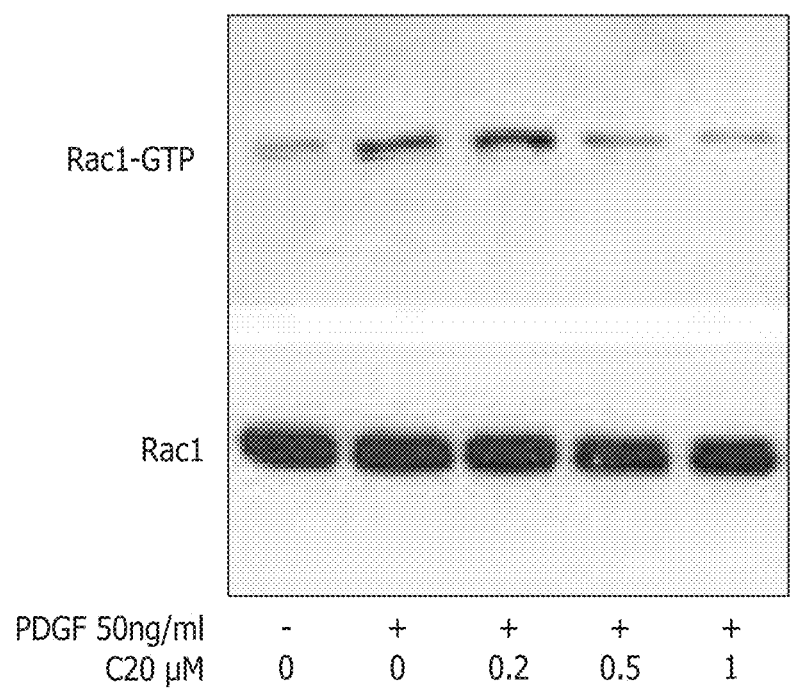
FIGS. 3A-3C depicts various properties of compound C20.
Figure 3B:
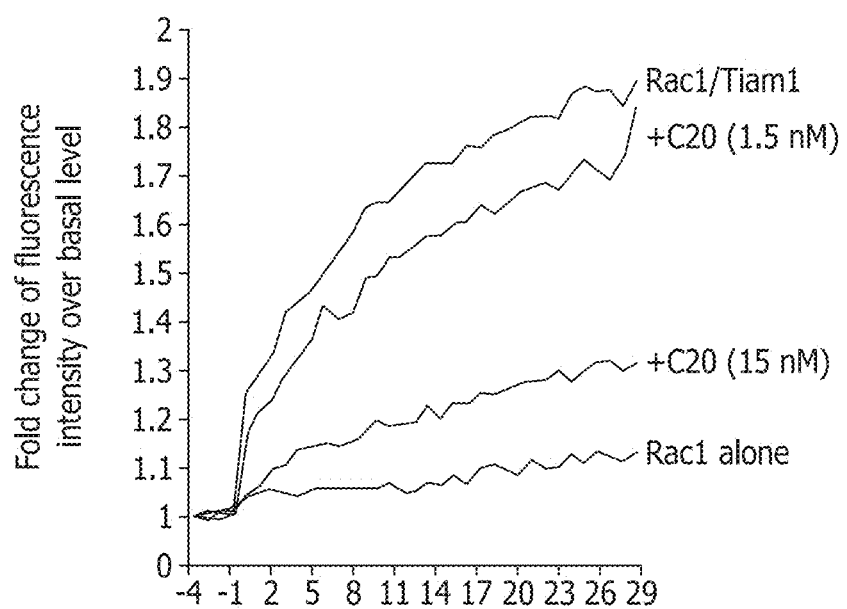
Figure 3C:
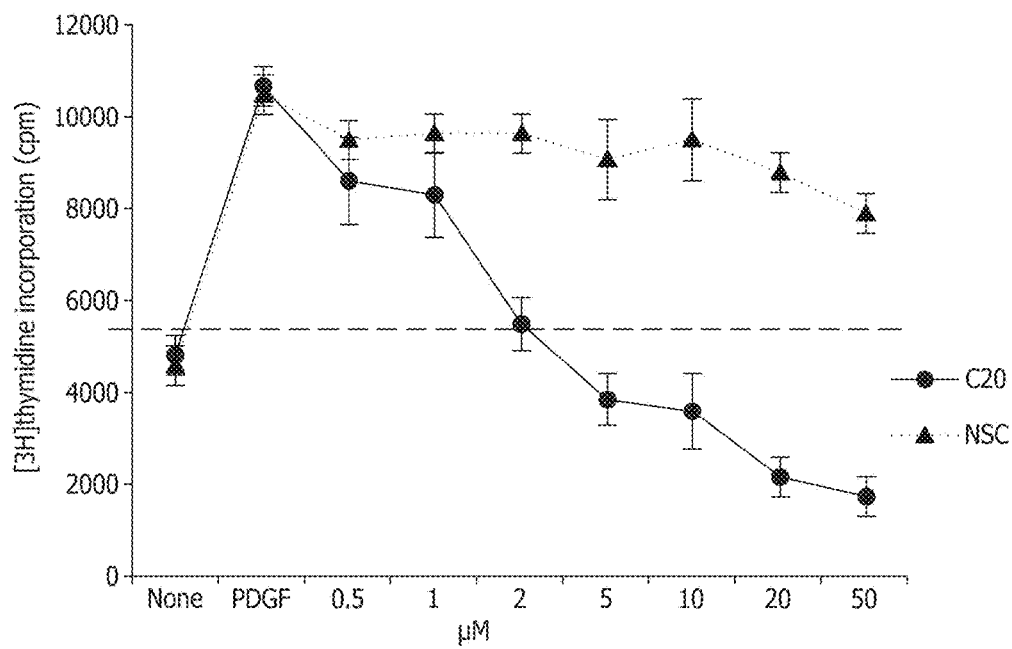

In initial screens assaying platelet derived growth factor (PDGF)-mediated proliferation in NF1-deficient Schwann cells, compound C20 (KM04569, Ryan Scientific) was identified. C20 inhibited Schwann cell proliferation at 2 µM and Rac1GTP activity at 0.5 µM (FIGS. 3A-C). The structure of C20 is shown below:

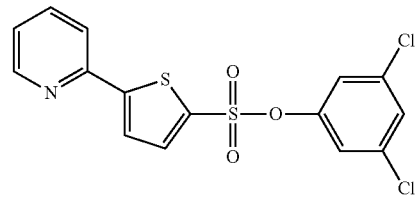 [SMILES: O=S(=O)(Oc1cc(Cl)cc(Cl)c1)c1ccc(-c2ccccn2)s1]

Based on the in silico design using the structure of NSC23766, it was predicted that C20 physically blocked Rac1-Tiam1 interactions. Rho-GEF exchange experiments using a commercially available kit that measures guanine exchange fluorescence quantification (Cat #BK100; Cytoskeleton, Inc., Denver, Colo.) were conducted to measure GEF inhibition by C20. A C20 dose-dependent GEF inhibition was found when incubating Tiam1 and Rac1 (FIG. 3B).

No effect of C20 on Ras-GTP activation or Akt phosphorylation was observed (data not shown). However, C20 mitigated Erk1/2 phosphorylation. Based on these results, compound C20 appears to have a selective affinity for blocking Rac1-Tiam1 interactions and, therefore, Rac1-GTP activity.

Example 2

In this Example, SAR analysis of compound C20 was conducted.

Figure 4:
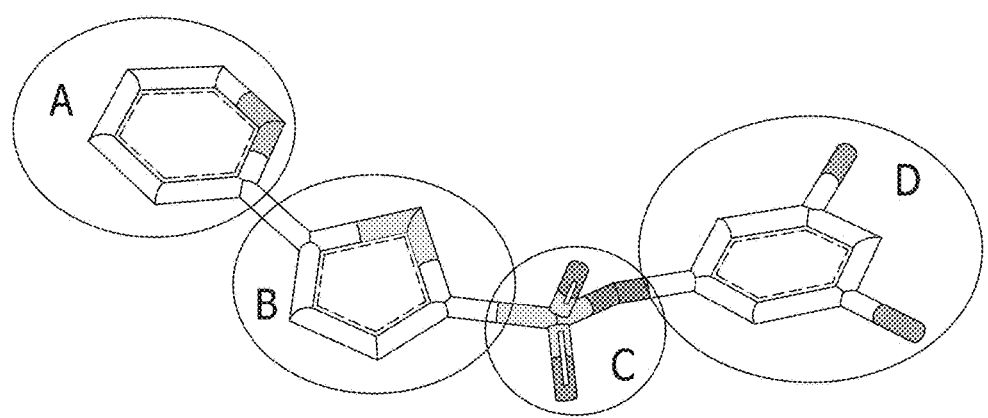
FIG. 4 depicts a 3D representation of compound C20.

Initial (SAR) studies were done with purchased compounds. For the purposes of SAR analysis, the structure of C20 (C$_{15}$H$_9$Cl$_2$NO$_3$S$_2$ with molecular weight 386) was divided into 4 structural or pharmacophore elements (herein referred to as A, B, C or D), as depicted below and in 3D in FIG. 4.

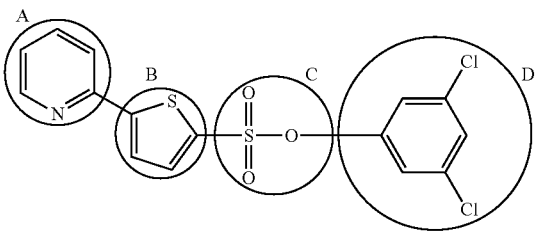

C20 can be synthesized directly from commercially available starting material. pharmacophore elements A, B and C are available in a single starting material and can be combined with a phenol as pharmacophore element D. The commercial availability of A-B-C facilitated the SAR analysis and permitted the rapid exploration of the D pharmacophore element from available phenols.

An improved potency and decreased cell toxicity was observed when both chlorine atoms were removed from the pharmacophore element D in the C20 structure. Substituting available anilines provided the corresponding amides, placing a nitrogen in the oxygen position in pharmacophore element C, thereby providing additional metabolic stability. Substituting benzyl alcohols or benzyl amines would allow extension of the D hydrophobic pharmacophore further into the binding site, thereby probing for additional binding interactions.

Several analogs of C20 were identified or synthesized and were then screened using the NF1−/− Schwann cell proliferation assay. The initial set of thirteen analogs were developed (Table 1; First SAR) by making substitutions in the C and D pharmacophore elements. However, these changes did not enhance the ability of these compounds to inhibit the platelet derived growth factor (PDGF)-mediated proliferation in NF1 deficient Schwann cells when compared to C20.

Figure 2:
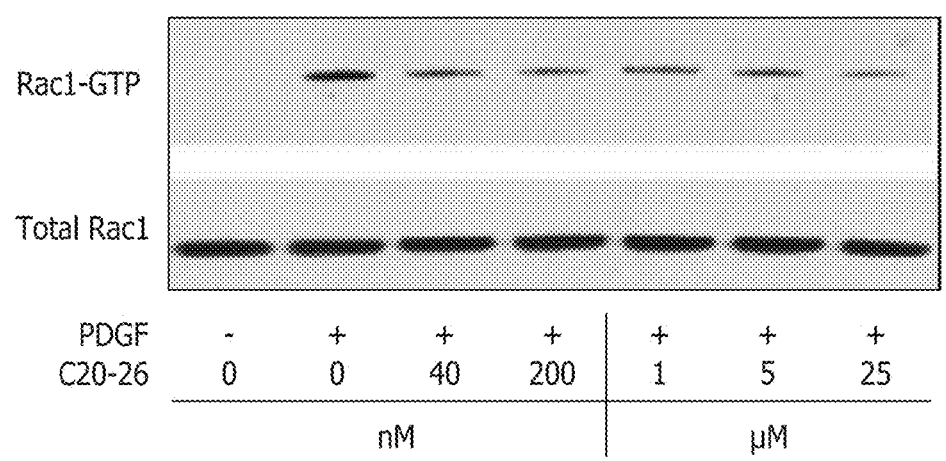
FIG. 2 depicts the inhibition of Rac1-GTP activity by compound C20-26. Compound C20-26 inhibits PDGF-mediated Rac1-GTP activity at 40 nM in murine-derived neurofibroma cells. After 24-hour starvation in 0.5% BSA/DMEM, Nf1−/−Schwann cells were pretreated with compound C20-26 at the indicated concentrations. Cells were then stimulated with 50 ng/mL PDGF for 2 minutes and harvested for immunoprecipitation.

A second SAR screen identified 12 additional compounds (Table 1), and of those, C20-26 was found to have a superior inhibitory effect on Rac1-GTP when compared to C20 (FIG. 2). C20-26 was found to be the most potent of the inhibitors in both SAR screens.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

I claim:

1. A compound for inhibiting Rac1, the compound having a structure of

A-B-C-D, wherein A is pyridyl, B is thiophene, C is sulfonate, and D is selected from the group consisting of phenyl, 3,5-dimethylphenyl, 3,5-methoxyphenyl, 3,5-difluorophenyl, 3,5-ditrifluoromethylphenyl, 3,5-dicarboxamidophenyl, 3,5-dicyanophenyl, 3,5-dimethylsufonylphenyl, and 4-trifluoromethylsulfonylphenyl.

2. The compound as set forth in claim 1, wherein A is pyridyl, B is thiophene, C is sulfonate, and D is phenyl.

* * * * *